Figure 1A:
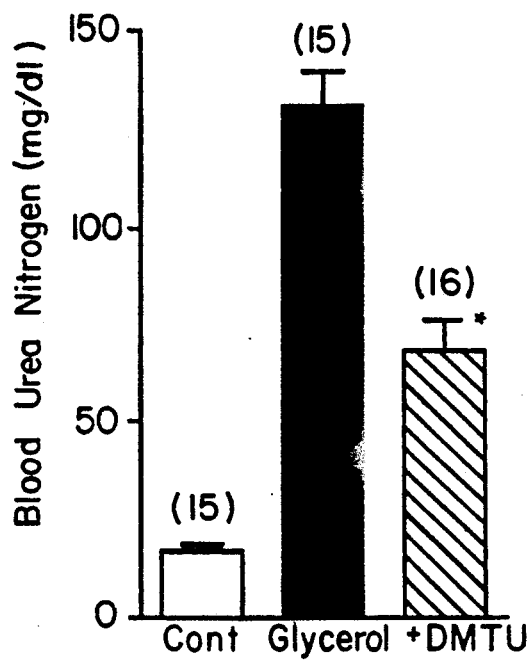

United States Patent [19]

Walker et al.

[11] Patent Number: 5,091,180

[45] Date of Patent: Feb. 25, 1992

[54] PROTECTION AGAINST RHABDOMYOLYSIS-INDUCED NEPHROTOXICITY

[75] Inventors: Patrick D. Walker, New Orleans; Sudhir V. Shah, Metairie, both of La.

[73] Assignee: Administrators of the Tulane Educational Fund, La.

[21] Appl. No.: 621,395

[22] Filed: Nov. 30, 1990

Related U.S. Application Data

[63] Continuation of Ser. No. 123,614, Nov. 20, 1987, abandoned.

[51] Int. Cl.$^5$ ............................................. A61K 37/50
[52] U.S. Cl. ................................. 424/944; 514/592; 514/708; 514/936; 514/568; 514/575; 514/2
[58] Field of Search ............... 424/94.4; 514/592, 708, 514/936, 568, 575, 2

[56] References Cited

PUBLICATIONS

Baud et al. Am. J. Physiol. 251: F765–F776.

Primary Examiner—Douglas W. Robinson
Assistant Examiner—Jean C. Witz
Attorney, Agent, or Firm—Pennie & Edmonds

[57] ABSTRACT

The present invention is directed to the in vivo use of compounds which prevent the generation of, effectively scavenge, or detoxify a reactive oxygen metabolite that mediates a toxic effect of rhabdomyolysis and myoglobinuria. The compounds of the invention can be used to prevent or reduce rhabdomyolysis-induced renal damage, and include but are not limited to free radical scavengers, iron chelators, oxidizable compounds, enzymes which metabolize reactive oxygen metabolites or their precursors, and biosynthetic precursors thereof.

14 Claims, 3 Drawing Sheets

PROTECTION AGAINST RHABDOMYOLYSIS-INDUCED NEPHROTOXICITY

This is a continuation of application Ser. No. 07/123,614 filed Nov. 20, 1987 abandoned.

TABLE OF CONTENTS

1. Introduction
2. Background of the Invention
   2.1. Rhabdomyolysis and Renal Failure
   2.2. Reactive Oxygen Metabolites
3. Summary of the Invention
   3.1. Definitions
4. Brief Description of the Figures
5. Detailed Description of the Invention
   5.1. Protective Agents
   5.2. Therapeutic Uses of Protective Agents
      5.2.1. Protection Against Renal Damage
6. Example: Prevention of Glycerol-Induced Acute Renal Failure in Rats

1. INTRODUCTION

The present invention is directed to the in vivo use of compounds that prevent the generation of, effectively scavenge, or detoxify a reactive oxygen metabolite that mediates a toxic effect of rhabdomyolysis or myoglobinuria. The compounds of the invention include agents which prevent the generation of, effectively scavenge, or detoxify free radicals such as the hydroxyl radical, or their metabolic precursors such as hydrogen peroxide and superoxide radical. In a specific embodiment of the invention, compounds that are hydroxyl radical scavengers can provide protection against the nephrotoxicity resulting from rhabdomyolysis or myoglobinuria. In another embodiment of the invention, compounds which are iron chelators can reduce renal damage due to the effects of rhabdomyolysis or myoglobinuria.

2. BACKGROUND OF THE INVENTION

2.1. Rhabdomyolysis and Renal Failure

In 1941, it was first noted that an association existed between skeletal muscle injury and the release of muscle cell contents into plasma (Bywaters and Beall, *Br. J. Med.* 1:427-432, 1941). This release of muscle cell contents (rhabdomyolysis) includes myoglobin, resulting in myoglobinemia and myoglobinuria, or myoglobin in the urine. In its most serious manifestation, rhabdomyolysis may ultimately result in acute renal failure (ARF). Rhabdomyolysis is not solely associated with direct muscle trauma or renal failure; the condition may be associated as well with non-traumatic causes such as prolonged strenuous exercise. Thus, myoglobinuria has also been shown to be connected with non-pathological conditions. It is estimated that about one-third of the patients with rhabdomyolysis will develop acute renal failure (Gaben et al. *Medicine* 61: 141-152, 1982). A list of a number of the possible causes for rhabdomyolysis provided in Table 1.

The exact mechanism by which ARF results from rhabdomyolysis has not yet been elucidated. The observed clinical association of ARF with intravascular hemolysis and skeletal muscle necrosis has led to the suggestion that the constituents of these tissues are toxic to the kidneys. Studies of the heme components in particular, i.e., myoglobin, hemoglobin and their derivations, have shown them to be extremely nephrotoxic when renal ischemia or systemic acidosis occurs.

The most commonly used model of myoglobinuric renal failure is produced by the subcutaneous or intramuscular injection of hypertonic glycerol (Hofstetter et al., in *Acute Renal Failure*, Brenner et al., eds., W. B. Saunders, p. 109, 1983). Following glycerol administration, muscle cell necrosis and myoglobinuria occur; in the early stages of ARF, there is a pronounced drop in renal blood flow (RBF), and a concomitant rise in renal vascular resistance. Also observed in the early phase of glycerol induced ARF is a fall in glomerular filtration rate. In the maintenance phase, although RBF may return to normal because of fluid expansion, GRF does not necessarily improve, indicating that its fall at this stage is not necessarily associated with the drop in RBF. The mediation of renal vasoconstruction in myoglobinuria ARF have not been established; the renin-angrotensive system haa been suggested, based on the observation that salt-loaded animals are resistant to glycerol-induced ARF. However, administration of an angrotensin II antagonist, or an angrotensin converting enzyme inhibitor, although effective in raising RBF, has little effect on blood urea nitrogen levels (BUN). Other vaso-active systems, such as prostaglandin, arginine, vasopressin and endotoxin, a component of the cell wall of gram negative bacteria have been indicated as possible contribution to the renal ischemia associated with rhabdomyolysis-myoglobinuric ARF. Alterations in glomerular capillary ultrafiltration coefficient may also be an early pathogenic effect in ARF, but no conclusive results have yet been observed. Thus, despite the intensive study directed in this area, the actual pathogneic mechanism which causes a drop in GRF is still unknown.

TABLE 1

| Causes of Rhabdomyolysis | |
|---|---|
| Increased Energy Consumption | Primary-muscle Injury |
| Exercise stress | Polymyositis |
| Amphetamine, LSD | Dermatomyositis |
| Delirium tremens | Trauma, crash |
| Convulsions | Burns |
| High-voltage shock | Infectious |
| Tetanus | Gas gangrene |
| Succinylcholine chloride | Tetanus |
| Fever | Leptospirosis |
| Malignant Hyperpyrexia | Viral influenza |
| Exercise-Induced heat stroke | Coxsackie infection |
| Heat cramps | Shigellosis |
| Decreased Energy Production-Genene | *Herbicola lathyri* bacteremia |
|  | Reye's syndrome |
| Affecting Carbohydrate Metabolism | Septic shock |
|  | Myxoma virus |
| Myophosphorylase deficiency | Pseudomonas bacteremia |
| α-glucosidase deficiency | Miscellaneous |
| Amylo-1,6-glucosidase deficiency | Venom |
| Phosphohexoisomerase deficiency | Snake bite |
|  | Hornet |
| Phosphofructokinase deficiency | Household brown spider |
|  | Sea-snake poisoning |
| Cytochrome Disturbances | Drugs |
| Diabetic acidosis | Heroin |
| Nonketotic hyperosmolar coma | Barbiturates |
| Affecting Lipid Metabolism | Propoxyphene |
| Carnitine deficiency | Methadone |
| Carnitine pulmityltansference deficiency | Glutethimide |
|  | Amphetamines |
| Various muscular dystrophies | Plasmocid |
| ↓ Energy Production Acquired | Licorice (glycyrrhizate) |
| K deficiency | Carbenoxolone |
|  | Amphotericin-B |

TABLE 1-continued

Causes of Rhabdomyolysis

| | |
|---|---|
| ↓ Glycogen formation | Diazepam |
| ↓ Insulin release with hyperglycemia | Codeine |
| | Epsilon aminocuprioc acid |
| Ethanol | Peanut oil (arachidonic acid) |
| Myxedema | Phencyclidine |
| Hypothermia | Other |
| Hypophosphatemia | Ingestion of quail fed on hemlock seed or sweet parsley |
| Diabetic ketoacidosis | |
| ↓ Oxygenation | Isopropyl alcohol |
| ↓ Muscle blood flow | Ethylene glycol |
| K deficiency | Huff disease |
| McArdle syndrome | Calciphylaxis (azotemic hyperparuthyroidism) |
| Postural vascular occlusion | |
| Arterial embolism | Acute schizophrenia |
| Prolonged surgery-(open heart) | Hypernatremia |
| | Insomnia |
| Carbon monoxide | 2,4-dichlorophenoxyacetic acid |
| Shock | Magnesium deficiency |
| Trauma | |
| Crash syndrome | |
| Conga drums | |
| Firearm recoil | |
| Karate | |
| Ice skating | |
| Jackhammer | |
| Sickle-cell trait | |

A number of conditions in which some form of tissue injury is observed have been suggested as being mediated by reactive oxygen metabolitis, including free radical species (see, e.g. Band et al., *Am. J. Physiol.* 251: F-765-F776, 1986; Weiss et al., *Lab. Invest.* 47: 5-18, 1982; Fantone et al., *Human Pathol* 16: 973-978, 1985; Weiss, *Acta Physiol. Scand.* 548: 9-37, 1986). Certain in vivo studies have demonstrated a protective effect of hydroxyl radical scavengers and/or iron chalatons in several models of tissue injury (Fox *J. Clin. Invest.* 74: 1456-1464, 1984; Trill et al., *Am. J. Pathol.* 119: 376-384, 1985; Take et al., *Am. Rev. Rsp. Dis.* 126: 802-806, 1982; Ward et al., *J. Clin Invest.* 76: 517-527, 1985; Ward et al., *J. Clin. Invest.* 72: 789-901, 1983; Flegrel et al., *Am. J. Physiol.* 115, 375-382, 1984; Johnson et al., *Lab. Invest.* 54: 499-506, 1986). Studies performed in connection with the present invention now suggest that reactive oxygen metabolites may play an important role in the pathology of rhabdomyolysis associated acute renal failure.

2.2. Reactive Oxygen Metabolites

The complete reduction of oxygen by the univalent pathway results in the formation of superoxide anion radical, hydrogen peroxide and hydroxyl radical (OH') as intermediates (Fridovich, I., 1976, Oxygen radicals, hydrogen peroxide and oxygen toxicity, in Free Radicals in Biology, Vol. I, Academic Press, pp. 239-278; Mastro, R. F., 1980, *Acta. Physiol. Scand. Supp.* 92: 153-168). These intermediates are too reactive to be tolerated in living tissue, and a variety of enzymatic mechanisms which can bypass the electron spin restriction of oxygen and accomplish the divalent and tetravalent reduction of oxygen to water have evolved. Thus, most of the oxygen consumed by respiring cells is utilized by cytochrome oxidase which reduces oxygen to water without releasing either superoxide or hydrogen peroxide (Fridovich, I., 1976, supra). Despite this, in respiring cells at least some reduction of oxygen occurs via the univalent path. In in vitro studies, the ability of microsomes and mitochondria to generate superoxide and hydrogen peroxide (Chance, B., et al., 1979, *Physiol. Rev.* 59: 527-605; Forman, H. J., and Boveris, A., 1982, Superoxide radical and hydrogen peroxide in mitochondria, in Free Radicals in Biology, Academic Press, pp. 65-90) and the ability of several agents to enhance this generation (Doroshow, J. H. and Davies, K. J. A., 1986, *J. Biol. Chem.* 261: 3068-3074) has been demonstrated.

In addition, the generation of reactive oxygen metabolite by phagocytic cells include neutrophils and monocytes has been well demonstrated (Fantone et al., *J. Am. Pathol.* 107: 397-418, 1982; Fantone et al., *Hum. Pathol* 16: 973-978, 1985; Weiss et al., *Lab. Invest.* 47: 5-18, 1982).

When the generation of superoxide and hydrogen peroxide is enhanced, superoxide and hydrogen peroxide may not only be directly cytotoxic, but, in addition, may interact (with iron as catalyst) by the Haber Weiss reaction to generate the hydroxyl radical (Hoe, S., et al., 1982, *Chem. -Biol. Interactions* 41: 7501; Aust, C. D., et al., 1985, *J. Free Radicals Biology & Medicine* 1: 3-25):

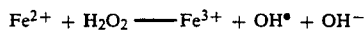

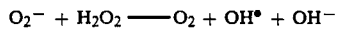

Several studies have shown that agents that enhance the generation of hydrogen peroxide and superoxide anion by mitochondria also enhance the generation of hydroxyl radical (Doroshow and Davies, supra; Komiyama, T., et al., 1982, *Biochem. Pharm.* 31(22): 3651-3656).

The enzymatic defenses against superoxide and hydrogen peroxide includes superoxide dismutase, catalase, and glutathione peroxidase. Superoxide dismutase converts the superoxide radical into hydrogen peroxide and molecular oxygen:

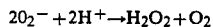

Two superoxide dismutases have been identified in mammalian tissues, a cytoplasmic copper-zinc and a mitochondrial manganese-dependent enzyme (reviewed in Fantone, J. C. and Ward, P. A., 1982, *Amer. J. Pathology* 107: 397-416; Fantone, J. C. and Ward, P. A., 1985, *Human Pathology* 16(10): 973-978; Fridovich, I., 1979, Superoxide dismutase: defense against endogenous superoxide radical, in Oxygen free radicals and tissue damage, *Ciba Symposium* 65: 77-85). The enzymatic mechanisms for cellular detoxification of hydrogen peroxide are catalase and glutathione peroxidase (reviewed in Fantone, J. C. and Ward, P. A., 1982, supra; Fridovich, I., 1976, supra; Maestro, R. F., 1980, *Acta. Physiol. Scand. Supp.* 92: 153-168; Chance, B., et al., 1979, *Physiol. Rev.* 59: 527-605). Catalase, a cytoplasmic heme-enzyme, catalyses the divalent reduction of hydrogen peroxide to water:

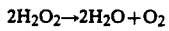

Glutathione peroxidase, a selenium-dependent enzyme, is effective at low concentrations of hydrogen peroxide and can also act upon lipid hydroperoxides, thus countering the toxicity of a wide range of peroxides (Lawrence, R. A. and Burk, F. R., 1976, *Biochem. Biophys. Res. Commun.* 71: 952-958). Recently, a seleniumindependent glutathione peroxidase activity which can detoxify organic peroxides but not metabolize hydrogen peroxide has been identified (Lawrence, R. A. and Burk, R. F., 1978, *J. Nutr.* 108: 211-215).

In addition to the enzymatic mechanisms, cellular detoxification also appears to be mediated by reduced glutathione (GSH). GSH, a tripeptide which occurs in high concentrations in virtually all mammalian cells, appears to function in the protection of cells against the effects of free radicals and reactive oxygen intermediates (e.g. peroxides) (Meister, A., 1983, *Science*, 22: 472-478; Meister, A. and Anderson, M. E., 1983, *Ann. Rev. Biochem.* 52: 711-60; Meister, A., 1984, *Hepatology* 4(4): 739-742; Andreoli, S. P., et al., 1986, *J. Lab. Clin. Med.* 108(3): 190-198; Jensen, G. L. and Meister, A., 1983, *Proc. Natl. Acad. Sci. U.S.A.* 80: 4714-4717; Dethmers, J. K. and Meister, A., 1981, *Proc. Natl. Acad. Sci. U.S.A.* 78(12): 7492-7496; Arrick, B. A., et al., 1982, *J. Biol. Chem.* 257(3): 1231-1237).

The cytotoxicity of reactive oxygen metabolites, including free radical species (e.g. superoxide and hydroxyl radicals) and other oxygen metabolites (e.g. hydrogen peroxide, hypochlorous acid) is well documented (Fantone, J. C. and Ward, P. A., 1982, *Am. J. Pathol.* 107: 397-418; Fantone, J. C. and Ward, P. A., 1985, *Hum. Pathol.* 16: 973-978; Weiss, S. J. and Lo-Buglio, A. F., 1982, *Lab. Invest.* 47(1): 5-18). In particular, recent in vivo studies have demonstrated the protective effect of hydroxyl radical scavengers and/or iron chelators (presumably by preventing the generation of hydroxyl radical by the iron-catalysed Haber Weiss reaction) in several models of tissue injury (supra). In addition, both in vitro and in vivo studies have suggested a role of glutathione in protecting against adriamycin (an anthracycline antibiotic) cardiotoxicity, presumably by its detoxification of oxidative free radicals (Olson, R. D., et al., 1981, *Life Sciences* 29: 1393-1401; Yoda, Y., 1986, *Cancer Res.* 46: 251). Some limited studies have examined the role of reactive oxygen metabolites in renal disease. We have shown that reactive oxygen metabolites affect several biological processes potentially important in glomerular diseases (Shah, S. V., 1984, *J. Clin. Invest.* 74: 393-401), and their role in neutrophil-mediated glomerular diseases has been demonstrated by others (Rehan, A., et al., 1984, *Lab. Invest.* 51: 396-403; Rehan, A., et al., 1985, Kidney Intl. 27: 503-511; Rehan, A., et al., 1986, *Am. J. Physiol.* 123(1): 57-66). In addition, reactive oxygen metobolites have been postulated to be important in ischemic acute renal failure (Paller, M. S., et al., 1984, *J. Clin. Invest.* 74: 1156-1164). However, the role of reactive oxygen metabolites in glycerol induced renal failure nephrotoxicity has not been previously examined.

3. SUMMARY OF THE INVENTION

The present invention is directed to the in vivo use of compounds, termed hereinafter "protective agents", which prevent the generation of, effectively scavenge, or detoxify a reactive oxygen metabolite (ROM) that counteracts a toxic effect of rhabdomyolysis. The protective agents of the invention include but are not limited to free radical scavengers, iron chelators, and enzymes which metabolize reactive oxygen metabolites, converting them to less toxic states and/or preventing the production of other toxic species. The protective agents also include oxidizable compounds which effectively detoxify the ROMs, exerting a protective effect by undergoing oxidation in lieu of important cellular components. Another group of protective agents includes any compounds (e.g. biosynthetic precursors) which increase the effective in vivo concentrations of endogenous protective agents.

The invention is based in part, on the discovery that the nephrotoxic effects of rhabdomyolysis (and the products produced thereby) in vivo are mediated by ROMs. The protective agents can be used therapeutically, in accordance with the present invention, before, during, or after rhabdomyolysis to prevent or reduce rhabdomyolysis-induced nephrotoxicity. In specific embodiments, hydroxyl radical scavengers or iron-chelators can be used to protect against renal damage. In another aspect of the invention, enzymes such as catalase and/or superoxide dismutase can be used to convert the reactive metabolites $H_2O_2$ and $O_2^-$ to less harmful products and to prevent the generation of other toxic metabolites. In particular embodiments, the iron-chelator deferoxamine, the hydroxyl radical scavenger dimethylthiourea, or glutathione biosynthetic precursors can be administered to protect against antibiotic rhabdomyolysis-induced nephrotoxicity.

3.1. Definitions

The following terms and abbreviations will have the meanings indicated:

Protective agent = A compound that prevents the generation of, effectively scavenges, or detoxifies a rhabdomyolysis-induced reactive oxygen metabolite which mediates a toxic effect.

OC = Oxidizable compound. A protective agent which detoxifies a reactive oxygen metabolite by undergoing oxidation by the reactive oxygen metabolite, in lieu of and preventing the detrimental oxidation of other cellular components.

BUN = blood urea nitrogen.
DMSO = dimethyl sulfoxide.
DMTU = dimethylthiourea
ROM = reactive oxygen metabolite.

4. BRIEF DESCRIPTION OF THE FIGURES

Figure 1B:
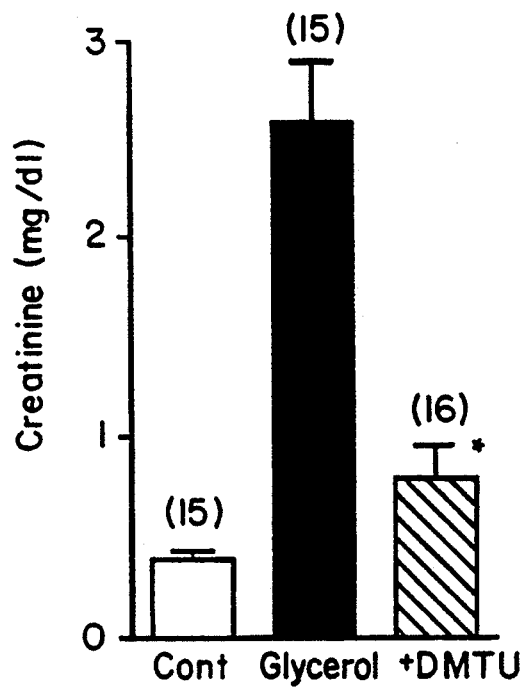

FIGS. 1A and 1B demonstrates the effect of the hydroxyl radical scavenger dimethylthiourea (DMTU) on glycerol-induced acute renal failure as measured by plasma urea nitrogen and creatinine. DMTU was administered in a dose of 500 mg/kg intraperitoneally (i.p.) just prior to the glycerol injection (50% glycerol, 8 ml/kg one half of the does in each hind limb muscle) followed by 125 mg/kg i.p. 8 hours later. The results (mean±SE) are from two separate experiments with the number of animals in each group shown in parenthesis. *$p < 0.05$ comparing the group treated with glycerol alone vs. glycerol+DMTU.

Figure 2A:
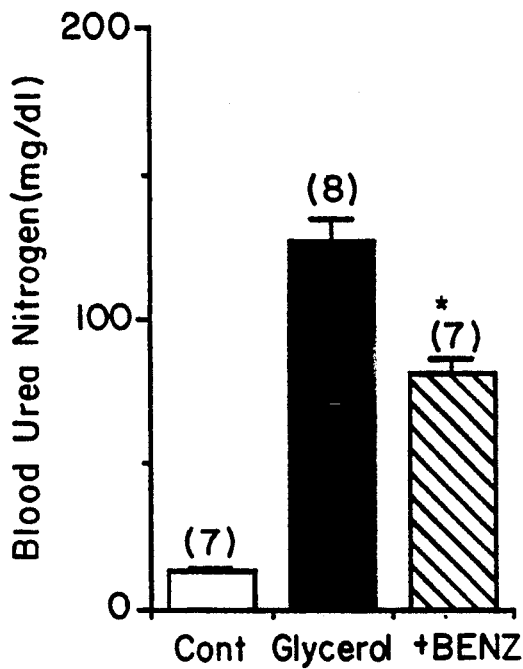
Figure 2B:
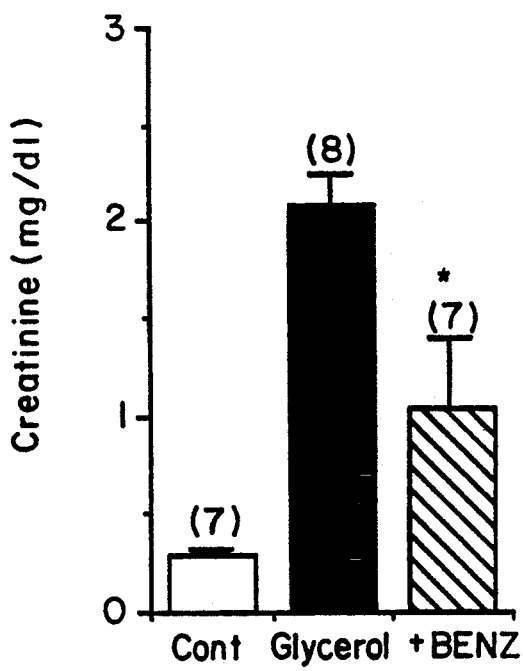

FIGS. 2A and 2B demonstrates the effect of the hydroxyl radical scavenger, sodium benzoate (150 mg/kg i.p. just before the glycerol injection and again 8 hours later) (BENZOATE) on glycerol-induced acute renal failure as measured by (FIG. 2A) blood urea nitrogen and (FIG. 2B) creatinine. The results (mean±SE) are from one experiment with the number of animals in each group shown in parenthesis. *$p < 0.05$ comparing the group treated with glycerol alone vs. glycerol+BENZ.

Figure 3A:
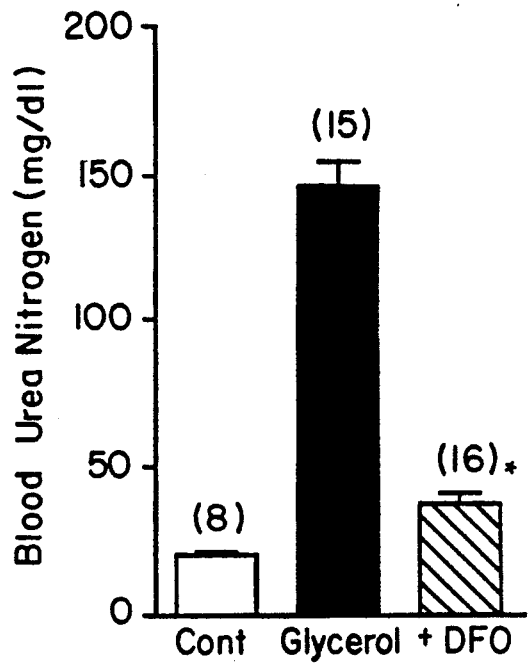
Figure 3B:
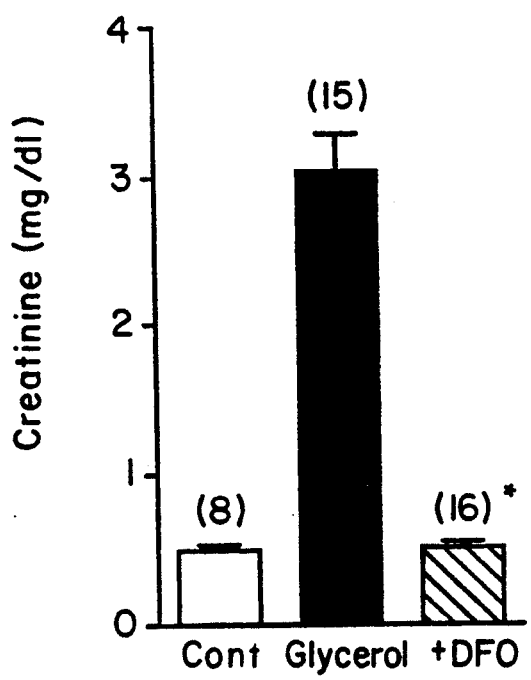

FIGS. 3A and 3B demonstrates the effect of an iron chelator on glycerol-induced acute renal failure. The iron chelator deferoxamine was administered intravenously in a dose of 30 mg/rat just prior to the glycerol injection. At the same time, deferoxamine was administered via an osmotic pump that was implanted subcutaneously. The drug was reconstituted in water at a concentration of 250 mg/ml, and the pumps (with a 2 ml capacity) delivered approximately 35 mg deferoxamine per rat per day at continuous rate of 5 $\mu$l/hr. The results (mean±SE) are from two separate experiments with the number of animals in each group shown in parenthesis. *$p < 0.001$ comparing the group treated with glycerol alone vs. glycerol+DFO.

5. DETAILED DESCRIPTION OF THE INVENTION

The present invention relates to the use of compounds in vivo that prevent the generation of, effectively scavenge, or detoxify a reactive oxygen metabolite (ROM) that mediates a toxic effect of rhabdomyolysis and associated by-products. The invention is based, in part, on the discovery that the nephrotoxic effects of rhabdomyolysis in vivo are mediated by ROMs. The compounds of the invention act by preventing the production of, by removing, or by preventing the detrimental reaction with cellular components of hydroxyl radicals, superoxide radicals, hydrogen peroxide, and other ROMS. These compounds shall be termed hereinafter "protective agents".

5.1. Protective Agents

The protective agents of the present invention are compounds that can be used in vivo to prevent toxic side effects such as renal damage caused by rhabdomyolysis. The protective agents exert their effect by preventing the generation of, by effectively scavenging, or by detoxifying ROMs, and include but are not limited to free radical and other ROM scavengers, iron chelating agents, and compounds (e.g. biosynthetic precursors) which increase the effective in vivo concentrations of endogenous protective agents. The scavengers of ROMs which may be used in the practice of the present invention include but are not limited to scavengers of hydroxyl radicals, superoxide radicals, hydrogen peroxide, and singlet oxygen. The hydroxyl radical scavengers of the present invention include but are not limited to dimethylthiourea, dimethyl sulfoxide, and sodium benzoate. The protective agents also include but are not limited to enzymes (e.g. superoxide dismutase, catalase, and glutathione peroxidase) which convert ROMs to less toxic states or metabolize ROMs (e.g. $O_2^-$ and $H_2O_2$) thus preventing the further generation of other ROMs. Another category of protective agents includes nonenzymatic, oxidizable compounds (termed hereinafter OCs) which effectively detoxify the ROMs by undergoing oxidation in lieu of important cellular components. Such OCs include but are not limited to thiols, e.g. glutathione. Because thiols are easily oxidized, they may be preferentially oxidized by the reactive oxygen metabolites, thereby protecting the tissues from oxidative damage. Molecules which are metabolic precursors of OCs can be administered in order to increase effective endogenous OC concentrations in vivo. For example, biosynthetic precursors of reduced glutathione can be used which include but are not limited to gamma-glutamylcysteine, gamma-glutamylcysteine disulfide, and gamma-glutamylcystine (Anderson, M. E. and Meister, E., 1983, Proc. Natl. Acad. Sci. U.S.A. 80: 707-711). The iron chelators of the present invention include compounds that bind iron which is necessary for the generation of toxic free radicals or their precursors, thus preventing such generation. Metabolic precursors of free radicals which the protective agents of the present invention can convert to less harmful products, include but are not limited to hydrogen peroxide and superoxide radical, which, if not converted by protective agents, can react to produce hydroxyl radicals. The ROM scavengers, iron chelators, and enzymes of the invention are molecules that can effect their protective function in vivo at the appropriate site of ROM generation or accumulation, without significant toxic effects. The protective agents for use in the present invention include but are not limited to the scavengers, OCs, metabolic precursors, iron chelators, and enzymes of Table I, infra.

TABLE II
AGENTS WHICH CAN BE USED TO PROTECT AGAINST TOXIC EFFECTS OF RHABDOMYOLYSIS

I. ROM SCAVENGERS, OCs, OR METABOLIC PRECURSORS THEREOF[1]

dimethylthiourea
dimethyl sulfoxide
sodium benzoate
tryptophan
azide
dabco
histidine
mercaptoalkylamines
2-mercaptoethylamine and derivatives
glutathione
3-aminopropanethiol
(3-mercaptopropylamine), 2-aminopropanethiol
1-amino-2-propanethiol
DL-trans-2-aminocyclohexanethiol and derivatives
2-(3-aminopropylamino)ethanephosphorothioic acid (WR 2721)
N-(2-mercaptopropionyl)-glycine
gamma-glutamylcysteine
gamma-glutamylcysteine disulfide
gamma-glutamylcystine
cysteine
cysteine derivatives:
cysteine methyl ester hydrochloride
cysteine ethyl ester hydrochloride
cysteine propyl ester hydrochloride
cysteine isopropyl ester hydrochloride
cysteine butyl ester hydrochloride
cysteine isobutyl ester hydrochloride
cysteine isoamyl ester hydrochloride
rutosidyl-2'-methylenecysteine
2,3-dimercaptopropanesulfonate (Unithiol)
Cleland's reagent and derivatives
bis(2-aminoethyl) disulfide (cystamine)
thioctic acid
2-aminoethyl 2-aminoethanethiolsulfonate
organic thiosulfates (Bunte salts)
2-aminoethanethiosulfuric acid
2-aminopropane-1-thiosulfuric acid
N-alkylated-2-aminoethanethiosulfuric acids
N-(4-phenylbutyl) aminoethanesulfuric acid and derivatives
2-guanidinoethanethiosulfuric acid
sodium cysteinethiosulfate
phosphorothioates and derivatives
sodium 2-aminoethanephosphorothioate
2-guanidinoethanephosphorothioate
3-guanidinopropanephosphorothioate
Other thioureas
thiourea
methylthiourea
ethylenethiourea
methylthiopseudourea
ethylthiopseudourea
$\alpha,\omega$-bis(thiopseudoureas)
5-ethylisothiuronium ethyl phosphine
2-aminoethylisothiuronium bromide hydrobromide (AET)
aminoethylisothiuronium adenine triphosphate (Adeturon)
bis(2-guanidinoethyl) disulfide (GED)

TABLE II-continued

AGENTS WHICH CAN BE USED TO PROTECT
AGAINST TOXIC EFFECTS OF RHABDOMYOLYSIS 2-aminobutylthiopseudourea dihydrobromide
thiazolines
thiazolidines and derivatives
gallic acid derivatives
  sodium gallate
  propyl gallate
  p-aminoacetophenone
  p-aminopropiophenone (PAPP)
II. IRON CHELATORS
  deferoxamine (deferoxamine B mesylate)
  2,3-dihydroxybenzoic acid
  diethylenetriaminepentaacetic acid (DETAPAC, DTPA)
  apolactoferrin (lactoferrin)
III. ENZYMES
  superoxide dismutase
  catalase
  glutathione peroxidase

[1]For a discussion of some of these compounds, see Kirk-Othmer, Encyclopedia of Chemical Technology, 3rd Ed., Vol. 19, 1982, John Wiley & Sons, New York, pp. 801-832.

5.2. Therapeutic Uses of Protective Agents

The protective agents of the present invention can be used to protect against the toxic side effects of traumatic or nontraumatic rhabdomyolysis or myoglobinuria, the toxic effect of which is mediated by a reactive oxygen metabolite. The protective agents may be administered subsequent to a traumatic muscular injury, or in conjunction with non-traumatic conditions which are frequently associated with rhabdomyolysis, in order to prevent or reduce toxicity. The protective agents can be administered by any of a variety of routes, including but not limited to intraperitoneal, intravenous, subcutaneous, oral, intranasal, intramuscular, etc. The protective agents can be delivered in various formulations. The present composition may be administered in any manner which is traditional for administration of chemotherapeutic agents, e.g., as capsules or tablets for oral administration. When oral preparations are desired, the compounds may be combined with the typical carriers, such as lactose, sucrose, starch, talc magnesium stearate, crystalline cellulose, methyl cellulose, hydroxypropyl cellulose, hydroxypropylmethyl cellulose, carboxymethyl cellulose, glycerin, sodium alginate, or gum arabic among others. For parenteral administration, suitable carriers are water or physiological saline.

In a particularly preferred embodiment, the protective agent is entrapped in a liposome, in order to prolong the effect of the protective agent in the body. The techniques for drug combination with liposomes are well known in the art.

Sample dosages required to achieve a therapeutic effect will generally be about 500 mg-1 g per dose with an iron chelator like deferoxamine. This would be administered parenterally typically in a 1 mg dose, followed by two 500 mg doses each within a 24 hour period. With liposome bound deferoxamine, a single 1 g dose is generally sufficient.

5.2.1. Protection Against Renal Damage

One of the detrimental side effects of the breakdown of skeletal muscle is nephrotoxicity caused by the release of cellular components. The protective agents of the present invention can be used before, during, or after exposure to rhabdomyolysis-causing conditions to protect against renal damage resulting from reactive oxygen metabolite production. Toxic effects on the kidney caused by rhabdomyolysis, that can be reduced or prevented by the protective agents include, for example, acute tubular necrosis and renal failure. In particular embodiments of the present invention, protective agents such as dimethylthiourea, sodium benzoate, dimethyl sulfoxide, deferoxamine, or 2,3-dihydroxybenzoic acid can be used to reduce the renal damage induced by traumatic or non-traumatic rhabdomyolysis. In one example of this embodiment, the iron-chelator deferoxamine can be formulated with a pharmaceutical carrier, and administered intramuscularly for the prevention of rhabdomyolysis-induced nephrotoxicity. In another embodiment, deferoxamine is first entrapped in a liposome, and then administered. In another particular embodiment, glutathione biosynthetic precursors can be used to increase the renal concentration of the endogenous OC glutathione. Studies have shown that the synthetic precursors gamma-glutamyl cysteine and gamma-glutamylcystine, when administered subcutaneously, will increase levels of glutathionine in the kidney (Anderson, M. E. and Meister, A., 1983, Proc. Natl. Acad. Sci. U.S.A. 80: 707-711). Careful monitoring of the patient's renal functioning can be done, by measurement of blood urea nitrogen (BUN), plasma creatinine levels, or any other standard techniques.

6. EXAMPLE: PREVENTION OF GLYCEROL-INDUCED ACUTE RENAL FAILURE IN RATS

The experiments detailed in the example sections infra demonstrate that treatment with compounds which prevent the generation of or effectively scavenge hydroxyl radicals effectively protects against glycerol-induced myoglobinuric acute renal failure in rats.

The purpose of the present study was to examine the effect of hydroxyl radical scavengers and an iron chelator on glycerol induced acute renal failure. Adult male Sprague-Dawley rats weighing 200-250 g and having free access to standard rat chow were used in these experiments. The rats were dehydrated for 24 hours, then injected with glycerol (under light ether anesthesia, 50% glycerol, 8 ml/kg one half of the dose in each hind limb muscle) and then allowed free access to water. The control animals were dehydrated as above except no injections were made. Twenty four hours after the glycerol injection, the rats were sacrificed, plasma obtained for the measurement of blood urea nitrogen (BUN), creatinine and kidneys obtained for histology. A marked increase in both BUN and creatinine was in rats injected with glycerol and this effect was reproducible and associated with no mortality at 24 hours. We first examined the effect of dimethylthiourea (DMTU), an hydroxyl radical scavenger, on glycerol-induced acute renal failure. The ability of DMTU to scavenge hydroxyl radical has been well established in in vitro studies. In addition, DMTU has been shown to achieve concentrations sufficient to scavenge hydroxyl radical in vivo (half-life-34 hours in rats). In addition, DMTU has been shown to achieve concentrations sufficient to scavenge hydroxyl radical in vivo (half-life-34 hours in rats). DMTU has been successfully lungs after exposure to a variety of injurious agents including: hyperoxia, thermal trauma, or, in isolated rat lung preparations, enzymatically generated oxygen metabolites and has been shown to be protective in an immune model of glomerular disease.

As shown in FIGS. 1A and 1B DMTU administered in a dose of 500 mg/kg intraperitoneally (i.p.) just prior to the glycerol injection followed by 125 mg/kg i.p. 8 hours later provided marked protection against glycerol-induced acute renal failure. In contrast to the effect of DMTU, urea (which is not an hydroxyl radical scavenger and serves as a control) administered in a does of 500 mg/kg intraperitoneally (i.p.) just prior to the glycerol injection followed by 125 mg/kg i.p. 8 hours later failed to provide any protection (glycerol alone, BUN 125±7, n=7; +urea, BUN 124±2, n=7). A second hydroxyl radical scavenger, sodium benzoate (150 mg/kg i.p. just before the glycerol injection and again 8 hours later) in doses similar to those used by others was also protective (FIGS. 2A and B).

Iron chelators, including deferoxamine and 2,3, dihydroxylbenzoic acid, have been shown to be protective in several in vivo models of tissue injury (supra).

The protective effect of iron chelators has been generally taken as evidence for the participation of hydroxyl radical in tissue injury because iron is critical in the generation of hydroxyl radical. It has been suggested that superoxide can act as a reductant for $Fe^{3+}$. The $Fe^{2+}$ then reduces the hydrogen peroxide to hydroxyl radical by the Fenton reaction. This reaction, commonly referred to as the metal-catalyzed Haber-Weiss reaction, may be summarized as follows:

$$Fe^3 + O_2^- \longrightarrow Fe^2 + O_2$$

$$Fe^2 + H_2O_2 \longrightarrow Fe^3 + OH^- + OH$$

$$O_2^- + H_2O_2 \longrightarrow O_2 + OH^- + OH$$

Indeed, in in vitro studies, the ability of deferoxamine to block the generation of hydroxyl radical has been well demonstrated. We therefore also examined the effect of the iron chelator deferoxamine on glycerol induced acute renal failure. The iron chelator deferoxamine B mesylate (DFO) (Desferal, Ciba-Geigy Corp., Summit, N.J.) was administered intravenously (i.v.) in a dose of 30 mg/rat just prior to the glycerol injection. At the same time, deferoxamine was administered via an osmotic pump (type 2ML1: ALZA Corp., Palo Alto, Calf.) that was implanted subcutaneously. The drug was reconstituted at a concentration of 150 mg/ml, and the pumps (with a 2 ml capacity) delivered approximately 30 mg of the DFO per rat per day at a continuous rate of 8.6 μl/hr. Previous studies have shown that constant plasma levels of the drug are maintained when the deferoxamine is administered by this route. Deferoxamine also provided a marked protective effect as shown in FIGS. 3A and B.

Although iron-mediated tissue injury could also be explained by a reaction involving the formation of the perferryl ion, in our study, the effectiveness of two hydroxyl radical scavengers suggests that the role of iron is related to its participation in the generation of hydroxyl radical. Taken together, the marked protective effect of both the hydroxyl radical scavengers and the iron chelators strongly implicate a role for hydroxyl radical in glycerol-induced acute renal failure.

What is claimed is:

1. A method for protecting against or reducing the renal toxicity of rhabdomyolysis comprising administering in vivo to a patient in need thereof an effective dose of at least one compound which substantially prevents the generation of, effectively scanvenges, or detoxifies a reactive oxygen metabolite which mediates a nephrotoxic effect of rhabdomyolysis.

2. The method according to claim 1 in which the compound comprises a free radical scavenger.

3. The method according to claim 2 in which the free radical scavenger comprises a hydroxyl radical scavenger.

4. The method according to claim 3 in which the hydroxyl radical scavenger comprises dimethylthiourea.

5. The method according to claim 3 in which the hydroxyl radical scavenger comprises dimethyl sulfoxide.

6. The method according to claim 3 in which the hydroxyl radical scavenger comprises sodium benzoate.

7. The method according to claim 1 in which the compound comprises an iron-chelating agent.

8. The method according to claim 7 in which the iron-chelating agent comprises deferoxamine.

9. The method according to claim 7 in which the iron-chelating agent comprises 2,3-dihydroxybenzoic acid.

10. The method according to claim 1 in which the compound comprises glutathione peroxidose.

11. The method according to claim 1 in which the compound comprises superoxide dismutase.

12. The method according to claim 1 in which the compound comprises catalase.

13. The method according to claim 1 in which administration is parenteral.

14. The method of claim 13 wherein administration is intramuscular.

* * * * *